(12) United States Patent
Van Herpen

(10) Patent No.: US 7,921,693 B2
(45) Date of Patent: Apr. 12, 2011

(54) PHOTO-ACOUSTIC SPECTROMETER APPARATUS

(75) Inventor: Maarten Marinus Johannes Wilhelm Van Herpen, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 578 days.

(21) Appl. No.: 11/994,451

(22) PCT Filed: Jun. 30, 2006

(86) PCT No.: PCT/IB2006/052198
§ 371 (c)(1), (2), (4) Date: Jan. 2, 2008

(87) PCT Pub. No.: WO2007/004168
PCT Pub. Date: Jan. 11, 2007

(65) Prior Publication Data
US 2008/0196477 A1    Aug. 21, 2008

(30) Foreign Application Priority Data
Jul. 6, 2005    (EP) .................................. 05300561

(51) Int. Cl.
*G01N 21/17*    (2006.01)
(52) U.S. Cl. ...................................... 73/24.02; 73/24.06
(58) Field of Classification Search ................ 73/24.02, 73/24.06
See application file for complete search history.

(56) References Cited

U.S. PATENT DOCUMENTS

| 3,893,771 | A | 7/1975 | Bell |
| 4,105,919 | A | 8/1978 | Bridges et al. |
| 4,657,397 | A | 4/1987 | Oehler et al. |
| 4,896,324 | A | 1/1990 | Ball et al. |
| 5,528,040 | A | 6/1996 | Lehmann |
| 6,363,772 | B1 | 4/2002 | Berry |
| 6,377,350 | B1 | 4/2002 | Paldus et al. |
| 7,012,696 | B2 * | 3/2006 | Orr et al. ..................... 356/454 |
| 7,259,856 | B2 * | 8/2007 | Kachanov et al. ............ 356/437 |
| 2004/0095579 | A1 | 5/2004 | Bisson et al. |
| 2004/0211905 | A1 | 10/2004 | Hancock et al. |

FOREIGN PATENT DOCUMENTS

WO    03100393 A1    12/2003

OTHER PUBLICATIONS

Fink T et al: "An Improved C02 Laser Intracavity Photoacoustic Spectrometer for Trace Gas Analysis", Review of Scientific Instruments, AIP, vol. 67, No. 11, pp. 4000-4004, 1996, XP000635858.

* cited by examiner

*Primary Examiner* — Daniel S Larkin

(57) ABSTRACT

A photo acoustic detection cell (6) is located within the optical cavity (3) of a cavity enhanced absorption spectroscopy apparatus (3,4,5). When a sample in the cell (6) absorbs radiation from a pulsed radiation beam coupled into the cavity (3) pressure waves are generated that are detected by a microphone (9). A detected signal (10) output by the microphone (9) may be processed to determine a value for the concentration of an absorber in the sample.

15 Claims, 1 Drawing Sheet

PHOTO-ACOUSTIC SPECTROMETER APPARATUS

Figure 1:
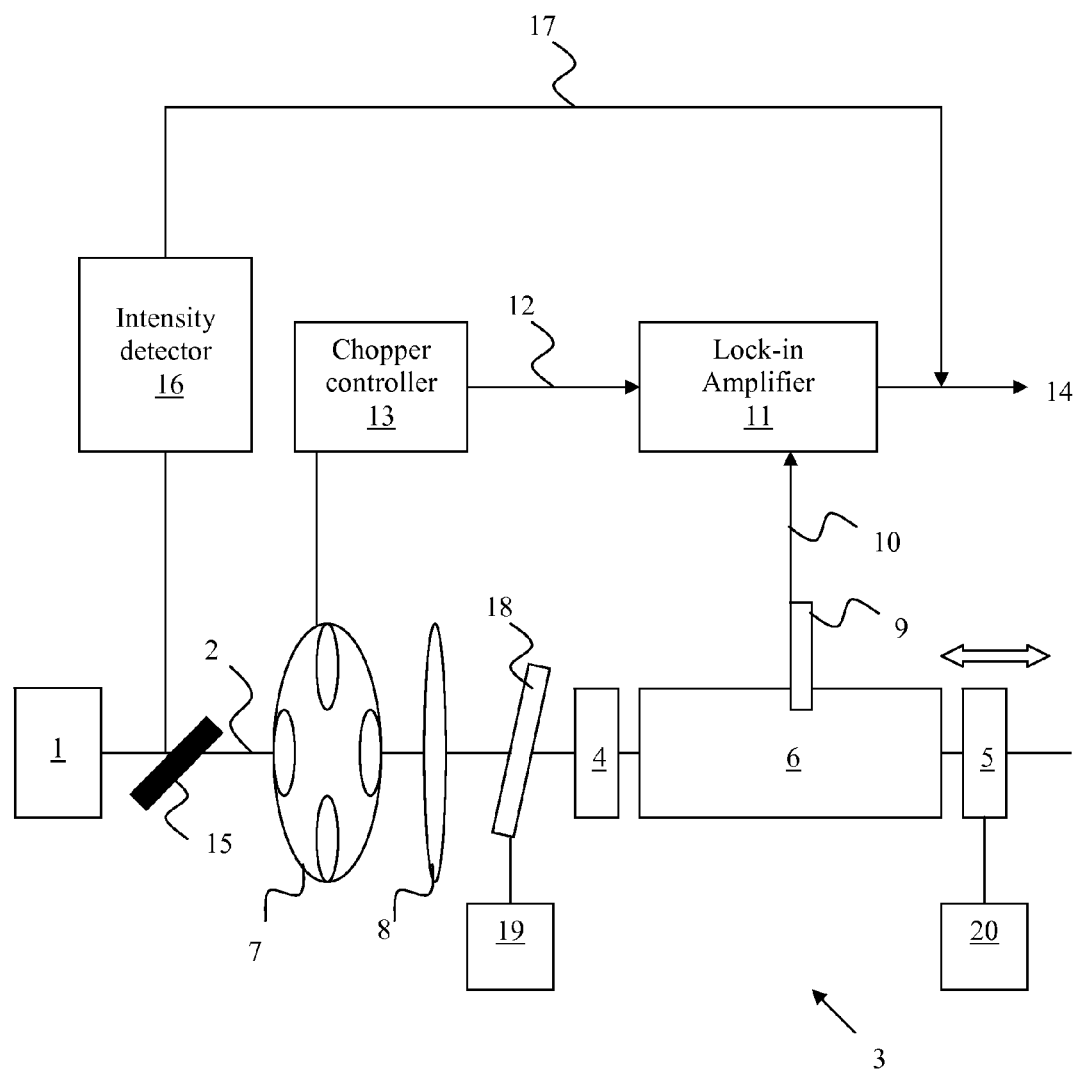

The present invention relates to a spectrometer apparatus and a spectroscopy method and in particular but not exclusively, a laser spectrometer apparatus and a laser spectroscopy method.

The use of laser absorption spectroscopy for analysing the composition of samples is well known. It may be used for example to detect pollutants in an air sample or to detect bio-markers in a breath sample. There are several known different laser absorption spectroscopy techniques.

Of these known techniques, direct absorption spectroscopy is the most basic. In this technique, a light source, an absorption cell and a light detector are used to analyse a sample contained in the absorption cell. When light from the light source passes through the absorption cell, gasses within the cell absorb some of the light. The light detector is located behind the absorption cell and is used to measure how much light has been absorbed. The concentration of the gas under detection can be calculated using the Lambert-Beer law, $$T = e^{-a \cdot c \cdot L} \quad (1)$$

where T is the transmittance of the gas, a is the absorption coefficient of the gas, c is the concentration of the gas, and L is the length of the absorption cell.

This equation shows that the total absorption increases if the path-length L increases and hence, for high measurement sensitivity, a long absorption cell should be used. To ensure high measurement sensitivity it is also possible to use a multi-pass absorption cell where mirrors are placed in front and behind the absorption cell, so that the light is reflected a few times through the absorption cell.

In photo-acoustic spectroscopy a laser beam is transmitted through a rotating blade, termed a chopper, which chops the beam into a series of light pulses at a pre-determined frequency. These pulses of light are transmitted through a Photo Acoustic Cell (PAC), in which a gas sample has been enclosed. If the laser wavelength is tuned to an absorbing molecular transition ($E_I$-$E_K$) of molecules in the sample, some of the molecules in the lower level $E_I$ will be excited into the upper level $E_K$. By collisions with other atoms or molecules these excited molecules may transfer their excitation energy into translational, rotational, or vibrational energy of the collision partners. At thermal equilibrium this process causes an increase of thermal energy, resulting in a rise of the temperature and pressure inside the cell. Every pulse of light thus causes an increase in gas pressure which then reduces again before the next pulse arrives. The pressure wave that is generated in this way may be heard by humans provided that the wave has sufficient amplitude and that the frequency (determined by the chopping frequency) lies within the hearing range of the human ear. However, very often a chopping frequency outside this range is used.

The PAC acts like an organ tube with its resonance frequency matched to the chopping frequency of the laser beam. It amplifies the generated sound wave, which is then transformed into an electronic signal by a microphone. A lock-in amplifier is used for further amplification and demodulation of this signal.

The lock-in amplifier is used to measure the amplitude and phase of the signal buried in noise. It achieves this by acting as a narrow bandpass filter, which removes much of the unwanted noise while allowing through the signal that is to be measured. The frequency of the signal to be measured and hence the bandpass region of the filter is set by a reference chopping frequency. In this way the sounds produced by the surroundings can be suppressed. The strength of the photo acoustic signal is given by:

$$S = \frac{2 N_i \sigma_{ik}}{fV} \Delta x (1 - \eta_k) P_L \Delta t S_m \quad (2)$$

in which $N_i$ gives the density of the absorbing molecules in $cm^{-3}$, $\sigma_{ik}$ gives the absorption cross section in $cm^2$, $\Delta x$ is the absorption pathlength, $\Delta t$ the cycle period, $P_L$ the laser power, $\eta_k$ gives the quantum efficiency (the ratio of emitted fluorescence energy to absorbed laser energy), f is the number of degrees of freedom that are accessible for each of the N molecules at the temperature T, V is the volume of the PAC and $S_m$ is the sensitivity of the microphone/PAC combination given in Volt/Pascal.

Equation 2 shows that the photo acoustic signal linearly depends on the concentration of the molecules. Furthermore, it also linearly depends on the power of the laser source, which means that a significant sensitivity can be gained using high power sources.

The advantage of this technique is that the setup is very simple. The disadvantage is that it requires a high laser power, if a high sensitivity is desired.

Cavity Ring—Down (CRD) spectroscopy is another absorption spectroscopy technique. It is a sensitive absorption technique in which the rate of absorption rather than the magnitude of the absorption of a light pulse confined in an optical cavity is measured. The sample is placed inside a high-finesse optical cavity consisting of two highly reflective mirrors. A short laser pulse is coupled into the cavity, the light is reflected back and forth inside the cavity and, every time that the light is reflected, a small fraction of this light leaks out of the cavity. Instead of measuring the total intensity of the light exiting the cavity, one determines the decay time by measuring the time dependence of the light leaking out of the cavity. In this way the rate of absorption can be obtained; the more the sample absorbs, the shorter is the measured decay time.

When a pulsed laser source is used, CRD is a relatively simple method. However, with a pulsed laser source the sensitivity of the detector is limited. In order to achieve high sensitivity, a continuous-wave laser source must be used. This however has the resultant disadvantage of making the setup very complicated, because it is necessary to bring the CRD cavity in resonance with the wavelength of the light source.

Cavity enhanced absorption (CEA) spectroscopy is a fairly new continuous wave (CW) sensitive absorption technique. It makes use of efficient multi-passing along the same optical path in a high-Q optical cavity. The laser light enters this optical cavity when the laser wavelength and the wavelength of one of the cavity-modes accidentally coincide. The time-integrated intensity of the light transmitted through the cavity is measured and is inversely proportional to the total cavity losses. As a result, the absorption coefficient of an absorber present in the cavity can be determined when the empty cavity losses are known.

In CEA spectroscopy the laser wavelength is not locked to the frequency of a cavity-mode. The cavity geometry is chosen such that the mode structure is very dense. During a measurement, both the laser wavelength and/or the wavelengths of the cavity-modes are dithered, resulting in a quasi-continuous in-coupling of light into the cavity. If the laser can be scanned repeatedly over a certain wavelength interval, as is the case for diode lasers, a 'raw' CEA spectrum can be obtained very rapidly (~1s) by summing several scans.

The CEA technique is a very simple method to use, and is also very suited for in-the-field applications. Unfortunately, the technique lacks sensitivity.

Embodiments of the present invention aims to alleviate the above-mentioned problems to provide an easy to use technique, that provides high sensitivity without the requirement of a high-power laser.

According to the present invention there is provided spectrometer apparatus comprising: a pulsed radiation beam generator for generating a pulsed radiation beam of pre-determined radiation wavelength; an optical cavity having a multitude of cavity modes each having a cavity mode wavelength; a dithering arrangement for dithering the radiation wavelength of the pulsed radiation beam and/or the multitude of cavity mode wavelengths such that the pulsed radiation beam quasi continuously couples into the optical cavity; a photo-acoustic cell located within the optical cavity for containing a sample to be analysed; and a detector for detecting pressure waves generated in the photo-acoustic cell when the sample absorbs radiation from the pulsed radiation beam and for producing a detector output signal that is processable to determine a value for the concentration of an absorber in the sample.

According to the present invention there is also provided A spectroscopy method comprising: generating a pulsed radiation beam of predetermined wavelength and directing the beam to an optical cavity having a multitude of cavity modes each having a cavity mode wavelength; dithering the radiation wavelength of the pulsed radiation beam and/or the multitude of cavity mode wavelengths such that the pulsed radiation beam quasi continuously couples into the optical cavity; detecting pressure waves generated in a photo-acoustic cell located within the optical cavity when a sample in the photo-acoustic cell absorbs radiation from the pulsed radiation beam to generate a detected signal and; processing the detected signal to determine a value for the concentration of an absorber in the sample.

An embodiment of the invention will now be described by way of example only with reference to the accompanying drawing in which:

FIG. 1 is a schematic diagram of a system embodying the present invention.

A continuous-wave laser source 1 emits a laser beam 2 of pre-selected wavelength towards a high Q laser cavity 3 defined by first 4 and second 5 cavity mirrors. The laser light enters the optical cavity 3 when the laser wavelength and the wavelength of one of the cavity modes of the cavity 3 coincide so that the beam 2 couples in the cavity 3.

The probability of coupling is enhanced by dithering the wavelength of the laser beam 2 and/or dithering the wavelengths of the cavity modes. The laser wavelength may be dithered by using a piezo-electric drive 19 to spatially modulate an intra cavity etalon 18 placed within the laser.

Dithering the wavelengths of the cavity modes may be achieved by spatially modulating one of the cavity mirrors, for example, by using a piezo-electric drive 20 to drive the second mirror 5 back and forth.

To further enhance the probability of coupling, the geometry of the cavity 3 may be selected so that its mode structure is very dense, or in other words, there is a relatively small wavelength spacing between the modes supported by the cavity 3.

In a preferred embodiment, the combined effect of the dense mode structure, laser wavelength dithering and cavity-mode dithering results in a quasi-continuous in-coupling of laser light 2 in the cavity 3.

In this respect, the embodiment functions as a cavity enhanced absorption spectrometer. As previously mentioned, it is known in the art of CEA spectroscopy that the time integrated measurement of the light intensity within the cavity 3 is inversely proportional to the total cavity losses. As a result, the absorption co-efficient of an absorber present in the cavity can be determined when the empty cavity losses are known. In known CEA spectroscopy systems, the techniques used to measure the light intensity within the cavity result in this type of spectroscopy being relatively insensitive to the concentration of absorber in the cavity.

Embodiments of the present invention use a photo acoustic spectroscopy technique to measure the light intensity within the cavity 3, in an effort to improve measurement sensitivity over that of standard CEA. To this end, in the embodiment shown in FIG. 1, a photo-acoustic cell 6 is placed within the optical cavity 3 and a rotary beam chopper 7 is located between the laser 1 and the first mirror 4. The rotary beam chopper 7 chops the laser beam 2 into a series of pulses by periodically blocking the laser beam 2.

Optionally, a lens 8 is placed between the chopper 7 and the first mirror 4 to focus the pulsed beam 2, between the two mirrors 4 and 5.

Absorption of light from the pulsed beam in the photo-acoustic cell 6 causes pressure waves to be generated in the cell 6 at the chopping frequency of the chopper 7. Preferably, by chopping the beam 2 at the resonance frequency of the photo-acoustic cell 6, these pressure waves are amplified into very strong waves, which are detected by a microphone 9 attached to the cell 6. The resultant signal 10 generated by the microphone 8 is sent to a lock-in amplifier 11 which uses a chopper reference frequency 12 provided by a chopper controller 13 to de-modulate the microphone signal 10 at the chopping frequency to generate an absorption signal 14 which is linearly proportional to the concentration of absorbing gas in the cell 6.

As well as being more highly sensitive than standard CEA, systems embodying the invention provide other advantages. For instance, compared to standard PAS, systems embodying the invention do not require a high powered laser to generate a strong enough photo-acoustic signal for high sensitivity measurements. Lower power lasers may be used instead. In addition, systems embodying the invention remain relatively easy to use compared to systems utilising CRD.

Optionally, a beam splitter 15 is located between the laser 1 and the chopper 7, is used to direct a small fraction of the laser beam 2 to an intensity detector 16. A detector signal 17 output by the detector 16 may be used to compensate the absorption signal 14 for variations in the intensity of the light beam 2.

In the above-described embodiment, two opposing mirrors define the cavity 3. Alternatively, the cavity may be defined by three mirrors arranged in a triangular ring design or four mirrors arranged in a bowtie ring design. Such designs have the advantage that the laser light incident on the first or entrance mirror does not reflect back towards the laser itself, which can cause feedback problems in some lasers.

Having thus described the present invention by reference to a preferred embodiment it is to be well understood that the embodiment in question is exemplary only and that modifications and variations such as will occur to those possessed of appropriate knowledge and skills may be made without departure from the spirit and scope of the invention as set forth in the appended claims and equivalents thereof. In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements.

The invention claimed is:

1. A spectrometer apparatus comprising:
   a pulsed radiation beam generator for generating a pulsed radiation beam of a pre-determined radiation wavelength;
   an optical cavity having a plurality of cavity modes, each cavity mode having a cavity mode wavelength;
   a dithering arrangement for dithering the radiation wavelength of the pulsed radiation beam and the plurality of cavity mode wavelengths such that the pulsed radiation beam quasi continuously couples into the optical cavity;
   a photo-acoustic cell located within the optical cavity for containing a sample to be analyzed; and
   a detector for detecting pressure waves generated in the photo-acoustic cell when the sample absorbs radiation from the pulsed radiation beam and for producing a detector output signal that is processable to determine a value for a concentration of an absorber in the sample.

2. The apparatus according to claim 1, wherein the pulsed radiation beam generator comprises:
   a radiation source for generating a continuous radiation beam; and
   a pulse generator located between the radiation source and the optical cavity for converting the continuous radiation beam into the pulsed radiation beam input to the cavity.

3. The apparatus according to claim 2, further comprising;
   a de-modulator for using a reference signal having a frequency equal to the pulse frequency of the pulsed radiation beam to demodulate the detector output signal to generate an absorption signal which is substantially linearly proportional to the concentration of the absorber in the sample.

4. The apparatus according to claim 1, wherein the pulse frequency of the radiation beam substantially matches a resonance frequency of the photo-acoustic cell.

5. The apparatus according to claim 1, further comprising:
   a beam splitter located between a source of the pulsed radiation beam and the optical cavity, the beam splitter being configured to direct a fraction of the radiation from the source to a radiation detector; and
   the radiation detector configured to output a compensation signal for use in compensating the absorption signal for variations in the intensity of the pulsed radiation beam.

6. A spectroscopy method comprising:
   generating a pulsed radiation beam of predetermined wavelength and directing the pulsed radiation beam to an optical cavity having a plurality of cavity modes, each cavity mode having a corresponding cavity mode wavelength;
   dithering the radiation wavelength of at least the pulsed radiation beam such that the pulsed radiation beam quasi continuously couples into the optical cavity;
   detecting pressure waves generated in a photo-acoustic cell located within the optical cavity when a sample in the photo-acoustic cell absorbs radiation from the pulsed radiation beam to generate a detected signal; and
   processing the detected signal to determine a value for a concentration of an absorber in the sample.

7. The method according to claim 6, further comprising:
   generating a continuous radiation beam; and
   converting the continuous radiation beam into the pulsed radiation beam input to the cavity.

8. The method according to claim 6, wherein the continuous radiation beam is converted into the pulsed radiation beam by a rotary chopper.

9. The method according to claim 6 wherein the pulse frequency of the radiation beam substantially matches a resonance frequency of the photo-acoustic cell.

10. The method according to claim 6, further comprising:
    using a reference signal having a frequency equal to the pulse frequency of the pulsed radiation beam to demodulate the detected signal to generate an absorption signal which is substantially linearly proportional to the concentration of the absorber in the sample.

11. The method according to claim 6, further comprising:
    generating a compensation signal for use in compensating the absorption signal for variations in the intensity of the pulsed radiation beam.

12. The method according to claim 6 further comprising focusing the radiation beam into the optical cavity.

13. The method according to claim 6, wherein the radiation source is a laser, the method further comprising spatially modulating an intra cavity etalon within the laser to thereby dither the radiation wavelength of the pulsed radiation beam.

14. The method according to claim 6 wherein the geometry of the cavity is arranged such that the spacing of cavity mode wavelengths is dense.

15. A spectroscopy method comprising:
    generating a pulsed radiation beam of predetermined wavelength and directing the pulsed radiation beam to an optical cavity having a plurality of cavity modes, each cavity mode having a corresponding cavity mode wavelength;
    dithering at least one of the radiation wavelength of the pulsed radiation beam and the plurality of cavity mode wavelengths such that the pulsed radiation beam quasi continuously couples into the optical cavity;
    detecting pressure waves generated in a photo-acoustic cell located within the optical cavity when a sample in the photo-acoustic cell absorbs radiation from the pulsed radiation beam to generate a detected signal;
    processing the detected signal to determine a value for a concentration of an absorber in the sample; and
    generating a compensation signal for use in compensating the absorption signal for variations in the intensity of the pulsed radiation beam, wherein generating the compensation signal comprises locating a beam splitter between a source of the pulsed radiation beam and the optical cavity to direct a fraction of the radiation from the source to a radiation detector to output the compensation signal.

* * * * *